United States Patent [19]

Halecky et al.

[11] Patent Number: 6,096,292
[45] Date of Patent: Aug. 1, 2000

[54] POLYMERIC DESENSITIZING COMPOSITIONS

[75] Inventors: Alan Halecky, West Orange; Michelle S. Kelly, Mantua, both of N.J.

[73] Assignee: Block Drug Company, Inc., Jersey City, N.J.

[21] Appl. No.: 09/123,344

[22] Filed: Jul. 28, 1998

[51] Int. Cl.⁷ .............................. A61K 7/16; A61K 7/18
[52] U.S. Cl. ............................................... 424/49; 424/52
[58] Field of Search ......................................... 424/49–58

[56] References Cited

U.S. PATENT DOCUMENTS

| | | |
|---|---|---|
| 4,002,732 | 1/1977 | Gault . |
| 4,217,342 | 8/1980 | Gaffar et al. . |
| 4,296,096 | 10/1981 | Pierce . |
| 4,645,662 | 2/1987 | Nakashima et al. . |
| 4,661,341 | 4/1987 | Benedict et al. . |
| 4,847,070 | 7/1989 | Pyrz et al. . |
| 4,861,539 | 8/1989 | Allen et al. . |
| 4,997,714 | 3/1991 | Farrar et al. . |
| 5,133,957 | 7/1992 | Suh et al. . |
| 5,135,396 | 8/1992 | Kuboki . |
| 5,139,768 | 8/1992 | Friedman . |
| 5,211,939 | 5/1993 | Turesky et al. . |
| 5,234,971 | 8/1993 | Imai et al. ........................... 433/228.1 |
| 5,270,031 | 12/1993 | Lim et al. . |
| 5,280,079 | 1/1994 | Allen et al. . |
| 5,330,746 | 7/1994 | Friedman et al. . |
| 5,374,417 | 12/1994 | Norfleet et al. . |
| 5,438,076 | 8/1995 | Friedman et al. . |
| 5,597,552 | 1/1997 | Herms et al. ......................... 424/49 F |
| 5,653,964 | 8/1997 | Herms et al. ......................... 424/49 F |
| 5,693,315 | 12/1997 | Bevilacqua ............................ 424/52 F |
| 5,797,749 | 8/1998 | Bertolotti et al. ................ 433/228.1 F |

*Primary Examiner*—Shep K. Rose

[57] ABSTRACT

A superabsorbent acrylic polymer is used to impart desensitizing properties to an oral composition for the treatment of hypersensitive teeth. The mouth feel of the composition is improved by incorporating therein a low molecular weight polyacrylic acid and a divalent salt such as zinc sulfate.

17 Claims, No Drawings

POLYMERIC DESENSITIZING COMPOSITIONS

BACKGROUND OF THE INVENTION

1. Field of the Invention

The invention relates to compositions for the treatment of dentinal hypersensitivity and methods for treating dentinal hypersensitivity.

2. Description of Related Art

Dentinal hypersensitivity can cause pain and discomfort when hypersensitive teeth are subjected to changes in temperature, pressure or chemical action. Without wishing to be bound by theory, a possible source of the hypersensitivity is that dental nerves are overexposed to oral stimuli through exposed tubules in the dentin of affected teeth. Dentin is a bony material in teeth that is usually covered by enamel above the gum line and cementum below the gum line. Enamel is very resistant to degradation when compared to cementum, and recession of the gums, periodontal disease and improper dental care can expose the cementum to hostile conditions in the mouth. The enamel or cementum may be removed through decay, injury, disease or other reasons, thereby exposing the dentin to external stimuli in the mouth.

Dentin generally contains channels, called tubules, that allow material and energy transport between the exterior of the dentin and the interior of the tooth where the nerve is located. One theory of dentinal hypersensitivity, called the hydrodynamic theory, suggests that exposure of these tubules to external stimuli can cause irritation of the nerve and lead to the discomfort of hypersensitivity. Although the exact mechanism of hypersensitivity is still under investigation, it has recently been shown that pain triggered by air currents is related to the number of exposed tubules per unit area of dentin. According to the hydrodynamic theory of dentin sensitivity, mechanical and thermal stimuli of the dentin surface induces mass or energy transport through the intratubular fluid. Such fluid movements induce pain in the intradental nerves located near the dentin/pulp border.

Treatment of hypersensitivity has usually taken the form of topical delivery systems, such as dentifrices, mouth rinses, gels and sealants. One long-time treatment has been a dentifrice containing strontium chloride as the active ingredient.

The hydrodynamic theory of hypersensitivity suggests that hypersensitivity may be treated by making the nerve in the tooth less sensitive to stimuli or by blocking or occluding the tubules to prevent or limit exposure of the nerve to external stimuli. Agents to make the nerve less sensitive are generally referred to as "nerve agents," and agents that fully or partially occlude tubules are referred to as "tubule blocking agents."

One way that nerve agents work is to interfere with the electrolyte balance near the nerve. The outer membranes of the nerve then do not "fire" as frequently or as strongly as an untreated nerve. Such agents include potassium nitrate, potassium chloride, and potassium bicarbonate.

Occlusion of tubules is an alternative method of treatment. Occlusion can be full or partial and may be permanent or temporary. The invention relates to a successful tubule blocking agent comprising an acrylic polymer.

Acrylic polymers generally have been used for a great variety of dental applications. These uses include desensitizing agents, anticalculus agents, thickeners, binder ingredients, and the like. See, for example, U.S. Pat. No. 4,217,342 to Gaffar et al., issued Aug. 12, 1980 (anticalculus agent); U.S. Pat. No. 4,296,096 to Pierce, issued Oct. 20, 1981 (gelling agent); U.S. Pat. No. 4,645,662 to Nakashima et al., issued Feb. 24, 1987 (polyacrylic binder in a dentifrice with an aluminum carboxylate desensitizer); U.S. Pat. No. 4,002,732 to Gault, issued Jan. 11, 1977 (binder for a "speckle"); U.S. Pat. No. 4,847,070 to Pyrz et al. issued Jul. 11, 1989 (anticalculus agent); U.S. Pat. No. 4,661,341 to Benedict et al., issued Apr. 28, 1987 (anticalculus agent); U.S. Pat. No. 5,374,417 to Norfleet et al., issued Dec. 20, 1994 (potassium Gantrez® salts as desensitizers); U.S. Pat. No. 5,330,746 to Friedman et al., issued Jul. 19, 1994 (hypersensitivity agent embedded in acrylic polymer for sustained release); and U.S. Pat. No. 5,438,076 to Friedman et al., issued Aug. 1, 1995 (solidifying methacrylate for sustained release of pharmacological agent). One acrylic polymer, a polyacrylic acid having a typical molecular weight from about 450,000 to about 4,000,000 sold under the trademark Carbopol™, has been reported as a tubule blocking agent in U.S. Pat. No. 5,270,031 to Lim et al., issued Dec. 14, 1993.

U.S. Pat. No. 5,211,939 to Turesky et al., issued May 18, 1993, reports the use of charged polystyrene beads as tubule blocking agents, and U.S. Pat. No. 4,634,589 to Scheller et al., issued Jan. 6, 1987 and U.S. Pat. No. 4,710,372 to Scheller et al., issued Dec. 1, 1987, report the use of apatite as a tubule blocking agent.

Despite ongoing work in the field of desensitizers, there remains a strong and long-felt need for an effective tubule blocking agent that is compatible with fluorides and other conventional dentifrice ingredients. The agent must work well yet not be distasteful or exhibit an undesirable mouthfeel. The agent must be stable for the typical shelf-life of the dentifrice and should not interfere with other agents that may be present in the delivery system, such as a dentifrice.

CARBOPOL® type polymers, in particulate form, are effective in occlusion, but these materials can exhibit unpleasant organoleptic properties when incorporated into a dentifrice. In addition, these agents require a strong shearing force during processing into dentifrice formulations. Attempts to modify the organoleptic properties of CARBOPOL® polymers, in particular, by the addition of metal salts and glycols, have proven to be only partially effective in correcting these deficiencies.

SUMMARY OF THE INVENTION

The principal object of the present invention therefore is to provide a tubule blocking agent that overcomes the organoleptic and processing difficulties found with many tubule blocking agents.

It is another object of the invention to provide new dentinal desensitization compositions that provide improved organoleptic properties to the formulations being employed.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a tubule blocking agent comprising certain acrylic polymers, known as superabsorbent polymers, which demonstrate good tubule occlusion while avoiding most of the organoleptic difficulties encountered with Carbopol® type polymers.

It is an advantage of the invention that unpleasant organoleptic qualities may be substantially eliminated in formulations containing an acrylic acid polymer desensitizing agent through the addition of a low molecular weight polyacrylic acid to the desensitizing formulation.

To further achieve the foregoing objects and in accordance with the purpose of the invention, the invention further provides a method for desensitizing a hypersensitive tooth comprising the step of topically administering a formulation comprising a superabsorbent acrylic polymer to the hypersensitive tooth. The invention also provides a method for desensitizing a hypersensitive tooth comprising the step of topically administering a formulation comprising a superabsorbent acrylic polymer and a low molecular weight polyacrylic acid to the hypersensitive tooth.

Other features and advantages of the present invention will become apparent from the following description of the invention.

DETAILED DESCRIPTION OF THE INVENTION

Reference will now be made in detail to the presently preferred embodiments of the invention.

In accordance with one aspect of the present invention, a superabsorbent acrylic polymer is used as a dentinal desensitizing agent. The agent can be incorporated into a dentifrice, gel, mouthwash, lozenge, mucal adhesive patch, gum or the like.

Superabsorbent acrylic polymers are well-known. They have been used for such diverse applications as diapers and artificial snow. These polymers are water-absorbent, yet water-insoluble, crosslinked polymers that generally have a gel capacity of at least 50 grams of deionized water per gram at 20° C. and often at least 100, 200 or more grams of water per gram dry weight of polymer at 20° C.

The polymers are typically prepared in the form of particles by polymerizing a water soluble monomer or monomer blend, for instance, acrylic acid, and causing the polymer to be crosslinked. The polymer thereby becomes insoluble in water. The polymerization can be carried out with a bifunctional unsaturated comonomer that will be copolymerized into the polymer backbone to provide crosslinking, or appropriate side chains can be selected to permit ionic crosslinking, e.g., using aluminum ions between pendant groups. Typical processes of preparation are described, for instance, in U.S. Pat. No. 4,861,539 to Allen et al., issued Aug. 29, 1989, U.S. Pat. No. 4,997,714 to Farrar et al., issued Mar. 5, 1991, and U.S. Pat. No. 5,280,079 to Allen et al., issued Jan. 18, 1994.

The polymer may be a homopolymer of acrylic acid or may be formed from a water-soluble blend of monoethylenically unsaturated monomers selected in known manner so that the final crosslinked polymer is water-absorbent. Such monomer blends may be nonionic, anionic, or cationic. Suitable cationic monomers are dialkylaminoalkylmethacrylates and acrylamides, generally in the form of acid addition or quaternary ammonium salts. Nonionic monomers that can be employed include methacrylamide and the like. At present, the preferred superabsorbing polymers are the crosslinked emulsion polymers of acrylic acid and copolymers of acrylic acid with acrylamide.

The particle size of the superabsorbent polymer of the present invention is generally from about 0.5 to about 2.0 microns before water absorption. Since the particles are irregular in shape, it will be understood by those skilled in the art that the term particle size is to be construed broadly. So long as the particles are effective as tubule blocking agents, the size will be appropriate to practice of the invention. The polymers can be made by any method known in the art, and commercially available superabsorbent polymers can be used. The most preferred polymer is a sodium polyacrylate emulsion polymer sold by Allied Colloids under the trade designation DP6-6984. This material has a variable particle size that can be controlled in a formulation by the addition of surfactants, glycols and metal ions to the formulation, as discussed in more detail below.

The superabsorbent polymers, in addition to providing desensitizing properties, also improve the organoleptic properties relative to the crosslinked polyacrylic acid of the Carbopol™ type. Nevertheless, a perception of gluiness in the mouth, which is believed to be caused by the formation of a muco-adhesive film by the polymer, remains. The addition of the usual variety of surfactants, glycols and metal ions has not ameliorated the sensation of gluiness. Surprisingly it was found that the perception of gluiness can be substantially eliminated by the addition of a low molecular weight polyacrylic acid. By low molecular weight is meant a molecular weight of less than about 2500 and preferably a molecular weight of about 1000 to 2000. Without being limited to theory, it is believed that because the number of molecular units in the low molecular weight polyacrylic acids is low, these polyacrylic acids, unlike the superabsorbent polymer, are not good film formers and therefore do not contribute a gluey sensation. In addition, the use of these low molecular weight polyacrylic acids does not diminish the tubule occluding activity of the superabsorbent polymer either per se or in the presence of common toothpaste additives such as abrasives, sodium fluoride, preservatives and flavoring agents. Preferred polyacrylic acids include Colloid 142, manufactured by Rhone Poulenc, this compound is a polyacrylic acid having a molecular weight of about 2000.

Some compositions incorporating the desensitizing polymer of the invention have not had acceptable levels of foaming and have shown a tendency to cause a perception of "clumping" in the mouth during brushing. This tendency may have been due to continued hydration of the polymer when exposed to saliva. These difficulties can be overcome by adding a small amount of a divalent salt to the composition. The cations in the salt bind to the anionic sites on the polymer and cause the polymer to contract. The contraction results in a lowering of the viscosity of the final dentifrice, which improves foaming. The cations also reduce the amount of hydration of the polymer, which in turn, reduces the perceived clumping. Without wishing to be bound by theory, we also believe that the polymer loses the cation in the tubule and swells, providing additional blocking of the tubule. Preferred cations include those nontoxic cations that do not precipitate fluoride in a dentifrice formulation, especially zinc and magnesium. The most preferred cation is zinc, and a preferred salt is zinc sulphate, especially the heptahydrate salt. The salt, if it is used, may comprise from about 5% by weight of the polymer to about 30% by weight of the polymer, preferably from about 10% by weight of the polymer to about 20% by weight of the polymer.

Those skilled in the art will appreciate that various delivery systems may be used in accordance with the invention. As non-limiting examples, the desensitizing agent can be formulated into a dentifrice, mouthwash, lozenge, buccal adhesive patch, oral spray, coatings or chewing gum.

Additional dentifrice, mouthwash or other oral health care ingredients may be incorporated into the composition of the invention. Dentifrices and mouthwashes are preferred delivery systems.

Preferably, a delivery system incorporating the invention will comprise a therapeutic amount of the superabsorbing polymer. This amount is an effective desensitizing amount of the polymer that, considering the method of delivery and the formulation, is sufficient to aid in desensitizing. For dentifrice applications, an effective desensitizing amount of the polymer is from about 0.1% to about 30% by weight of the dentifrice, preferably from about 1% to about 15% by weight of the dentifrice and most preferably from about 2% by weight to about 12% by weight of the dentifrice. Within this most preferable range, a dentifrice preferably comprises from about 3% to about 8% by weight of the dentifrice, and more preferably from about 4% to about 6% by weight of the dentifrice. A therapeutic amount is not necessarily an amount that will completely close all exposed tubules in a single administration. Rather, a therapeutic amount is an amount that will serve to reduce hypersensitivity in a tooth significantly with regular use. Thus, a therapeutic amount can be a level that blocks and thereafter continues to block a significant amount of exposed tubules with continued treatment. Those skilled in the art will recognize that other delivery systems may have differing levels of desensitizing material incorporated to provide a therapeutic amount of desensitizing agent based, in part, on the form of the delivery system and on the time of exposure of the desensitizing agent to the hypersensitive tooth as a result of using a particular delivery system. Generally, however, the desensitizing material will comprise from about 1% to about 30% by weight of a delivery system, preferably from about 2% to about 15% by weight of the delivery system, and more preferably from about 3% to about 8% by weight of the delivery system.

A delivery system may also comprise other materials in accordance with the invention. A dentifrice, for example, may contain materials for cleaning the teeth and for other purposes. The dentifrice, for example, may include at least one foaming agent such as sodium lauryl sarcosinate and sodium lauryl sulfate, although a combination of two foaming agents is preferred. The dentifrice may also include an abrasive. While any number of well-known abrasives are acceptable for use with the invention, we have found that one silica abrasive, Tixosil 73, interacted with the polymer to form a lumpy dough-like mass. Calcium pyrophosphate and Sylodent, two other silica abrasives, however, provided excellent dentifrices. A dentifrice may also contain a fluoride source, such as sodium fluoride, stannous fluoride or sodium monofluorophosphate, flavorings, sweeteners, preservatives and other ingredients commonly found in a dentifrice.

A mouthwash incorporating the desensitizing agent of the invention may contain typical mouthwash ingredients and solvents, such as water, alcohol, and poloxamers such as the Pluronic series of poloxamers. Other ingredients found in mouthwashes, including menthol, thymol and other essential oils, flavorants, sweeteners, and preservatives may also be used with the invention. The amount of desensitizing agent should, however, be regulated to provide acceptable mouthwash organoleptic qualities.

In order to further illustrate the present invention, non-limiting examples are set forth below. In these examples, as throughout the specification and claims, all temperatures are in degrees centigrade and all parts and percentages are by weight, unless otherwise indicated.

EXAMPLES 1–4

Dentifrice formulations were prepared using the ingredients set forth in Table 1. The dentifrices were made by slowly adding the polymer, sodium polyacrylate emulsion polymer sold by Allied Colloids under the trade designation DP6-6984, to deionized water (about 50–60° C.) with overhead stirring. Intense shearing is not required to disperse the polymer. Mixing was continued for about 15 minutes. Sodium fluoride is added to the dispersion and mixing is continued. The zinc salt is added followed by Colloid 142, sodium saccharin and methyl paraben. After another 15 minutes of mixing, the surfactants and abrasives are added and the mixture is whip mixed to the appropriate consistency.

TABLE 1

Dentifrice Formulations of Examples 1–4

| INGREDIENT | Weight Percent | | | |
|---|---|---|---|---|
| | Ex. 1 | Ex. 2 | Ex. 3 | Ex. 4 |
| Superabsorbent sodium polyacrylate emulsion polymer | 4.5 | 5.0 | 6.0 | 5.0 |
| Zinc sulfate (% as zinc ion) | 0.5 | 0.75 | 0.75 | 1.0 |
| Sodium fluoride | 0.34 | 0.25 | 0.25 | 0 |
| Sylodent 700 | 10.0 | 10.0 | 10.0 | 10.0 |
| Flavor | 0.3 | 0.3 | 0.3 | 0.3 |
| Colloid 142 | 5.0 | 5.0 | 5.0 | 5.0 |
| Methyl paraben | 0.1 | 0.1 | 0.1 | 0.1 |
| Sodium saccharin | 0.3 | 0.3 | 0.3 | 0.3 |
| Hamposyl L30 | 1.1 | 1.1 | 1.1 | 1.1 |
| Sodium lauryl sulfate | 1.5 | 1.5 | 0 | 0 |
| Water | q.s. 100 | q.s. 100 | q.s. 100 | q.s. 100 |

EXAMPLES 5–8

The formulations of Examples 1–4 were tested using the method described by Pashley (J. Periodontology, vol. 55, no. 9, p. 522, September 1994), which is also described in U.S. Pat. No. 5,270,031 to Lim et al., issued Dec. 14, 1993. The disclosure of that patent is hereby incorporated herein by reference in its entirety.

In this method, intact human molars free from caries and restorations are sectioned perpendicularly to the long axis of the tooth with a metallurgical saw into thin sections of about 0.4 to about 0.6 mm thick. Sections containing dentin and free of enamel are obtained for testing and are then etched with an ethylenediamine tetraacetic acid solution to remove the smear layer. The disc is mounted into the split chambered device described by Pashley which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs are wetted with human saliva to approximate the intraoral condition. The apparatus includes a gas capillary tube mounted on a ruler or other measuring instrument and an air bubble is injected into the glass capillary tube. By measuring the displacement of the bubble as a function of time, fluid flow through the dentin disc can be measured.

Following measurement of the baseline fluid flow in the dentin disc, an experimental dentifrice is applied to the external surface with a nylon brush. After a defined period of brushing, the experimental material is rinsed off, and the post-application hydraulic conductance is measured. In this fashion, the ability of various experimental materials both alone and as components of dentifrice systems can be tested for the ability to obstruct fluid flow in the dentinal tubules. The percent flow reduction induced by brushing with the experimental materials can then be calculated.

The percent fluid flow reduction using the dentifrice formulations of Examples 1 through 4 is shown in Table 2.

TABLE 2

Percent Flow Reduction of Examples 1–4

| Formulation | After Application |
|---|---|
| Example 1 | −92.3 |
| Example 2 | −83.5 |
| Example 3 | −93.4 |
| Example 4 | −98.1 |

EXAMPLE 9 (Prophetic)

A mouthwash in accordance with the invention may be made by mixing the ingredients in Table 3.

TABLE 3

Mouthwash Formulation of Example 9

| INGREDIENT | WEIGHT % |
|---|---|
| Dispersion of DP6-6984 | 70% |
| Alcohol 190 Proof (Grain Alcohol) | 10% |
| Pluronic F-127 | 2% |
| Flavor | 0.3% |
| Menthol | 0.02% |
| Water | q.s. to 100% |

EXAMPLE 10 (Prophetic)

A chewing gum in accordance with the invention may be made using the formulation in Table 4. The chewing gum base will be softened at 65° C. using a sigma blade mixer, cooled to 60° C. and ⅗ of the sorbitol powder and calcium saccharin will then be added, followed by the glycerin. Then ⅕ of the sorbitol powder, ½ of the lecithin and the superabsorbent polymer will be added. After cooling to 50° C., the rest of the sorbitol powder, lecithin, and flavor will be added. The mixture may then be rolled into patties and cut into strips.

TABLE 4

Chewing Gum Formulation of Example 10

| INGREDIENT | WEIGHT % |
|---|---|
| Chewing Gum NOVA Base "A" | 24.64% |
| Glycerin | 1% |
| Calcium saccharin | 0.06% |
| Sorbitol powder | 53.5% |
| Lycasin | 13% |
| Lecithin | 0.8% |
| Flavor | 1% |
| DP6-6984 | 6% |

EXAMPLE 11

A lozenge in accordance with the invention was prepared having the formulation set forth in Table 5. The sorbitol and xylitol were heated at 165° C. until the base started to thicken. The combination was cooled to 140° C. and the citric acid added. After cooling to 100° C., the gelatin was added and after cooling to 850° C., the flavor and superabsorbent polymer was added. Cooling was continued and a seed crystal of sorbitol was added to start crystallization. The mixture was poured into molds to form lozenges.

TABLE 5

Lozenge Formulation of Example 11

| INGREDIENT | WEIGHT % |
|---|---|
| Sorbitol | 81.5% |
| Xylitol | 6% |
| Citric Acid | 0.4% |
| Flavor | 0.1% |
| Gelatin | 7% |
| Superabsorbent polymer | 5% |

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An oral composition for desensitizing teeth having tubules with exposed openings, comprising:
   a desensitizing amount of a water absorbent, water-insoluble, crosslinked acrylic polymer having a gel capacity of at least 50 grams deionized water per gram dry polymer at 20° C. and an average particle size of less than the openings of said tubules.

2. The composition of claim 1, wherein said desensitizing agent has a gel capacity of at least 100 grams deionized water per gram dry polymer at 20° C.

3. The composition of claim 2, wherein said desensitizing agent is an emulsion acrylate polymer.

4. The composition of claim 3, wherein said emulsion polymer is a sodium polyacrylate polymer.

5. The composition of claim 1, wherein said emulsion polymer is a sodium polyacrylate emulsion polymer.

6. The composition of claim 1, further comprising a polyacrylic acid.

7. The composition of claim 6, wherein said polyacrylic acid has a molecular weight of up to about 2500.

8. The composition of claim 7, wherein said low molecular weight polyacrylic acid has a molecular weight of from about 1000 to about 2000.

9. The composition of claim 1, further comprising a divalent salt.

10. The composition of claim 9, wherein said divalent salt is selected from the group consisting of magnesium salts and zinc salts.

11. The composition of claim 10, wherein said divalent salt is zinc sulfate.

12. The composition of claim 6, further comprising a divalent salt.

13. The composition of claim 12, wherein said divalent salt is selected from the group consisting of magnesium salts and zinc salts.

14. The composition of claim 13, wherein said divalent salt is zinc sulfate.

15. The composition of claim 14, further comprising a source of fluoride.

16. The composition of claim 1, wherein said water absorbent, water-insoluble, crosslinked acrylic polymer has an average particle size of about 0.5 to 2.0 microns before water absorption.

17. A method for desensitizing teeth having tubules with exposed openings by applying thereto an oral composition comprising a desensitizing amount of a water absorbent, water-insoluble, crosslinked acrylic polymer having a gel capacity of at least 50 grams deionized water per gram dry polymer at 20° C. and an average particle size of less than the opening of said tubules.

* * * * *